United States Patent
Chow et al.

(10) Patent No.: US 6,816,793 B2
(45) Date of Patent: Nov. 9, 2004

(54) METHOD FOR PREDICTING FLOW PROPERTIES OF POWDERS

(75) Inventors: Kwok Yui Chow, Mississauga (CA); Danielle Marie Lockhart, Mississauga (CA); Andrew Giuseppi Guido Tallevi, Mississauga (CA)

(73) Assignee: SmithKline Beecham Corportion, Philadelphia, PA (US)

( * ) Notice: Subject to any disclaimer, the term of this patent is extended or adjusted under 35 U.S.C. 154(b) by 0 days.

(21) Appl. No.: 10/311,563
(22) PCT Filed: Jun. 29, 2001
(86) PCT No.: PCT/GB01/02948
§ 371 (c)(1), (2), (4) Date: Dec. 16, 2002
(87) PCT Pub. No.: WO02/01162
PCT Pub. Date: Jan. 3, 2002

(65) Prior Publication Data
US 2003/0176981 A1 Sep. 18, 2003

Related U.S. Application Data
(60) Provisional application No. 60/214,943, filed on Jun. 29, 2000.

(51) Int. Cl.[7] ............................ G01N 31/00; G01F 1/00; G01F 7/00
(52) U.S. Cl. ........................................ 702/30; 702/45
(58) Field of Search ....................... 702/30, 45; 73/863, 73/863.03, 863.41, 863.52, 863.56, 863.71

(56) References Cited

U.S. PATENT DOCUMENTS

| 5,448,476 A | 9/1995 | Kurokawa | 702/2 |
| 5,583,304 A | 12/1996 | Kalidindi | 73/863.56 |

Primary Examiner—Michael Nghiem
(74) Attorney, Agent, or Firm—Robert J. Smith

(57) ABSTRACT

A method for predicting flow properties of one or more materials proposed for processing in a system that requires good flow properties to operate successfully includes identifying a plurality of key flow points along a system, for each key flow point so identified, characterizing the type of flow occurring at that key flow point, for each key flow point, selecting a flow test relevant for modeling the type of flow occurring at that key flow point, providing a plurality of material samples wherein each material sample has a different composition, blend and/or concentration of ingredients, for each key flow point, modeling the type of flow occuring at that key flow point by conducting the flow test selected for that key flow point on each material sample to produce a plurality of test result values, wherein each test result value is a function of one of the flow tests conducted and of the material sample tested by that flow test, and ranking each material sample based on a calculated average of the test result values to determine which of the material samples tested has optimal overall flow properties for the system as compared against the other material samples.

23 Claims, 2 Drawing Sheets

METHOD FOR PREDICTING FLOW PROPERTIES OF POWDERS

This application is filed under 35 U.S.C. §371 as the United States National Phase Application of International Application No. PCT/GB01/02948 filed Jun. 29, 2001 claiming priority from United States Provisional Application No. 60/214,943 filed Jun. 29, 2000, the disclosures of which are incorporated herein by reference in their entirety.

TECHNICAL FIELD

The present invention generally relates to powder flow testing and analysis. More specifically, the present invention relates to a method for predicting the flow properties of powders based on a ranking of data derived from one or more powder flow tests.

BACKGROUND ART

In many processes or systems involving powder materials, especially pharmaceutical manufacturing processes, the material being processed must possess good flow properties in order for the manufacturing process to be successful. In the case of pharmaceutical processes, the material generally constitutes a formulation or blend of active ingredients as well as excipients. The excipients are usually inert substances (e.g., gum arabic, starch and the like) which serve as a vehicle for the active ingredients, or as lubricants, glidants, and bulking components. Poor flow characteristics of such formulations can result in equipment stoppages, clogged outlets, flooded compartments, and other conditions that disrupt the flow of the material during processing. One example of an important pharmaceutical process in which good flow properties are critical is the compression of powders into tablets that require uniform, consistent dosages and compositions. Powder compression can involve known process steps such as funneling, avalanching, tumbling, plug drop and the like.

The widespread use of powders in the pharmaceutical industry has given rise to a variety of methods for characterizing powder flow. Much research has been directed toward attempting to correlate the various measures of powder flow to manufacturing properties. It is believed that the multitude of test methods developed thus far is a result of the fact that powder flow behavior is multifaceted and complex. The pharmaceutical scientist often utilizes one or more of the standard tests to assess the flowability potential of sample powder materials and formulations. For a given manufacturing process and a given active drug substance or compound, such tests are employed to evaluate the optimal blend of active ingredients and excipients constituting the bulk quantity to be processed. It is well documented that the various flow tests generally accepted and commonly employed to date often do not correlate well with observed behavior on a development or production scale. One reason is that none of the tests reflect an intrinsic property of the powder being tested. In other words, each test is strongly dependent upon its respective methodology. There is a growing awareness, therefore, that because powder flow in general is a complex phenomenon, no single, simple test method can adequately characterize the wide range of flow properties observed for pharmaceutical powders.

Examples of basic, conventional flow tests are as follows. One popular test is the static angle of repose test. This test measures the "angle of repose," which can be defined as the constant, three-dimensional angle relative to a horizontal base that is assumed by a cone-like pile of material formed by any of several different methods. A lower angle of repose value indicates better powder flow. The angle of repose is formed by permitting powder to drop through a funnel onto a fixed, vibration-free base that includes a retaining lip to retain a layer of powder on the base. The height of the funnel is varied during the test in order to carefully build up a symmetrical cone of powder. Typically, the funnel height is maintained approximately 2 to 4 cm from the top of the powder pile as it is being formed in order to minimize the impact of falling powder on the tip of the cone. Alternatively, the funnel could be kept fixed while the base is permitted to vary as the pile forms. The angle of repose is determined by measuring the height of the powder cone and calculating the angle of repose $\forall$ from the following equation:

$$\tan(\alpha) = \frac{\text{height}}{1/2 \text{ base}}$$

One variation of this test is the drained angle of repose test, wherein an excess quantity of material positioned above a fixed diameter base is allowed to "drain" from the container. The drained angle of repose is determined from the cone of powder formed on the base. Another variation is the dynamic angle of repose test, in which a cylinder is filled and rotated at a specified speed. The dynamic angle of repose is the angle formed by the flowing powder.

It is believed that the angle of repose is essentially a measure of interparticulate friction, or resistance to movement between particles. Experimental difficulties arise in the use of this test due to segregation of material and consolidation or aeration of the powder as the cone is formed. Also, the peak of the cone of powder can be distorted by the impact of the powder falling from above, although this can be minimized somewhat by carefully building up the cone. In addition, the design of the base upon which the cone is formed influences the angle of repose. The provision of a fixed diameter base having a protruding outer edge can ameliorate this latter influence by ensuring that the cone of powder is formed on a retained layer of powder. Of course, if a powder of a given formulation is not capable of forming a symmetrical cone, this test is entirely inappropriate. Thus, although widely accepted as being valuable in predicting manufacturing problems, the angle of repose test has nonetheless been criticized on the grounds of lack of reproducibility and inconsistency in its ability to correlate with manufacturing properties or other measures of powder flow.

Another popular test for predicting powder flow characteristics measures the compressibility index or the closely related Hausner ratio. The test involves measuring the bulk or aerated density $V_a$ of a powder in a graduated cylinder, placing the cylinder on a tap density tester such as a Vanderkamp TAP DENSITY TESTER™, and measuring the "tapped" density $V_f$ of the powder, i.e., the density of the powder after tapping the cylinder a number of times (e.g., 200) until no further volumetric changes occur. A lower compressibility index value indicates better powder flow. One of the following calculations is then made:

$$\text{compressibility index} = 100 \times \left(\frac{V_a - V_f}{V_a}\right)$$

$$\text{Hausner ratio} = \frac{V_a}{V_f}$$

The values obtained as a result of this test are believed to be measures of the cohesiveness of a powder as it forms an arch in a hopper and the ease with which such an arch could be broken. In one variation, the rate of consolidation is also, or alternatively, measured. Factors influencing the methods used to obtain the compressibility index and the Hausner ratio include the diameter of the cylinder used, the number of times the powder is tapped to achieve the tapped density, the mass of material used in the test, and rotation of the sample during tapping.

Another type of test entails monitoring the rate of flow and/or change in flow rate of a powdered material through an orifice in order to obtain a measure of flowability and an indication of the effects of glidants, granule size and type of granulating agent on powder flow. The "flow through the orifice" test is useful only for free-flowing, non-cohesive materials. Either mass flow rate or volumetric flow rate can be measured, and done so either continuously or discretely. It is generally recommended that the container employed for this test be a vibration-free cylinder with a circular orifice. The size and shape of the container and orifice are important experimental variables. The diameter of the cylinder is recommended to be greater that two times the diameter of the orifice, while the diameter of the orifice is recommended to be greater than six times the diameter of the particles to be tested. A hopper could also serve as the container where representative of flow in a manufacturing situation. A funnel is not recommended since its stem would affect the flow rate. The test might involve the use of empirical equations that relate flow rate to the orifice diameter, particle size, and particle density.

A diverse array of shear cell methods have also been developed, and are considered to offer a greater degree of experimental control and provide a large amount of useful flow data. The parameters generated include the yield loci representative of shear stress-shear strain relationship, the angle of internal friction, the unconfined yield strength, and the tensile strength, as well as derived parameters such as the flow factor. In a typical shear cell test, a cylindrical shear cell is split horizontally to form a shear plane between a lower stationary base and the upper moveable portion of a shear cell ring. After powder bed consolidation in the shear cell, the force necessary to shear the powder bed by moving the upper ring is determined. Variations include annular and plate-type shear cell designs.

Another test involves avalanching methods, for which an Amherst Process Instruments AERO-FLOW™ device can be employed. Approximately 20 grams of material are loaded into a translucent drum, and the drum is rotated slowly at the rate of 120 seconds per revolution. A photocell array detector measures the total number of avalanches, and the average time between avalanches is calculated. A lower average time between avalanches indicates better powder flow.

A further test involves the use of a vibrating spatula or trough, such as a Hierath Automated Systems ISO-G4107, which cascades powder onto a mass balance interfacing with the vibrating spatula. Approximately 100 mL of powder is placed behind a removable gate 3 inches from the rear of the spatula and the vibration amplitude is set at 40%. The gate is removed and the mass of accumulated powder is recorded at 10-second intervals. Steeper slopes of mass accumulated vs. time plots represent better powder flow.

Finally, several variations of each of these basic methods described in detail hereinabove have been developed.

While attempts have been made to standardize and improve the various test methodologies, there remains a long-felt need for developing a method for accurately predicting the flow properties that powders can be expected to exhibit when processed in a given system.

DISCLOSURE OF THE INVENTION

The present invention provides a novel approach to assessing the flow properties of powders such as pharmaceutical materials. A fundamental principle of the present invention is a recognition that, not only is powder flow difficult to analyze with just one flow test or even a combination of flow tests, but accurate prediction of powder flow must take into account the different types of flow occurring in a given process or system at certain steps, or key points, of the process or system. The present invention accounts for these different flow types, and models each key point or system step by conducting a test that replicates the flow type observed at that particular key point. The specific test utilized for the corresponding key point can be a conventional test or any new test yet to be developed. A test is conducted for each flow point and for each candidate powder formulation under inquiry. After conducting each test on each proposed formulation, a ranking of the different formulations is determined. To enhance the utility of the present invention, the ranking can be based on a weighted average of the test results. Thus, the weighting factor used for a particular test result can be made equal or skewed, depending on the relative importance of each key point within the context of the overall system. As a result of the inventive method, one of the candidate powder formulations is identified as possessing the most promising flow properties for the particular system in which the powder is to be processed.

Preliminary studies have shown that the present inventive approach provides a superior and highly relevant prediction of flow during the compression of tablets, as compared to the mere use of one or more conventional tests to model an entire system.

According to one aspect of the present invention, a method is provided for predicting flow properties of one or more materials, in a case where such materials are proposed for processing in a system which requires good flow properties in order to operate successfully. The method comprises identifying a plurality of key flow points along the system and for each key flow point, characterizing the type of flow occurring at that key flow point and selecting a flow test relevant for modeling the type of flow occurring at that key flow point. A plurality of material samples are provided wherein each material sample has a different composition, blend or concentration of ingredients. For each key flow point, the type of flow occurring at that key flow point is modeled by conducting the flow test selected for that key flow point on each material sample to produce a plurality of test result values. Each test result value is a function of one of the flow tests conducted and of the material sample tested by that flow test. Each material sample is ranked based on a calculated average of the test result values to determine which of the material samples tested has optimal overall flow properties for the system as compared against the other material samples.

The test result values for each flow test conducted can be normalized by adjusting the test result value having the best ranking by a factor that sets that test result value to unity, and adjusting the other test result values obtained from that flow test by the same factor to convert the other test result values to reduced values equal to less than unity.

A weighting factor can be assigned to the test result value produced by each flow test conducted. The weighting factor is based on an assessed significance of the key flow point modeled by that flow test relative to the other key flow points identified for the system, such that the step of ranking each material sample is based on a weighted average of the test result values.

According to another aspect of the present invention, a method is provided for predicting flow properties of one or more materials wherein an overall ranking each of material sample is generated to predict the flow properties that each material sample will exhibit during processing of the material sample in the system. The following equation can be utilized:

$$\text{overall rank for powder } (X) = [\text{Test \#1 score} \times (1/N) \times WF_1] + \ldots + [\text{Test \#N score} \times (1/N) \times WF_N],$$

wherein (X) designates one of the material samples tested; "N" represents the total number of flow tests conducted; "Test #1 score" is the test result value obtained from conducting a first one of the plurality of flow tests corresponding to a first one of the key flow points identified; "$WF_1$" is a weighting factor optionally assigned to the Test #1 score based on an assessed significance of the first key flow point relative to the other key flow points; "Test #N score" is the test result value obtained from conducting an $N^{th}$ one of the plurality of flow tests corresponding to an $N^{th}$ one of the key flow points identified; and "$WF_N$" is a weighting factor optionally assigned to the Test #N score based on an assessed significance of the $N^{th}$ key flow point relative to the other key flow points.

According to yet another aspect of the present invention, a method is provided for predicting flow properties of one or more powder formulations proposed for processing in a system which requires good powder flow properties to operate successfully. The method includes identifying a plurality of key powder flow points along a system. For each key flow point, the type of flow occurring at that key flow point is characterized and a powder flow test relevant for modeling the type of flow occurring at that key flow point is selected. A plurality of powder samples are provided wherein each powder sample has a different composition, blend or concentration of ingredients. For each key flow point and for each powder sample, the type of flow occurring at that key flow point is modeled by conducting the powder flow test selected for that key flow point to produce a plurality of test result values. Each test result value is a function of one of the powder flow tests conducted and of the powder sample tested by that powder flow test. Each powder sample is ranked based on a calculated average of the test result values to determine which of the powder samples tested has optimal overall flow properties for the system as compared against the other powder samples.

The system under inquiry can include a tablet forming system including a hopper, a funnel fluidly communicating with the hopper, a feed frame fluidly communicating with the funnel, and a die table fluidly communicating with the feed frame.

According to a further aspect of the present invention, a pharmaceutical product is formed from a powder formulation predicted to exhibit optimized powder flow in a pharmaceutical product manufacturing system. The optimized powder formulation is determined by one of the ranking processes as described and claimed herein.

It is therefore an object of the present invention to provide a method for predicting the flow properties of one or more powders in a given system with a greater degree of accuracy, relevancy and validity than heretofore accomplished.

It is another object of the present invention to provide a method for predicting the flow properties of powders which produces a ranking of powders for use in selecting a candidate powder formulation for further development.

Some of the objects of the invention having been stated hereinabove, other objects will become evident as the description proceeds when taken in connection with the accompanying drawings as best described hereinbelow.

DETAILED DESCRIPTION OF THE INVENTION

Figure 1:
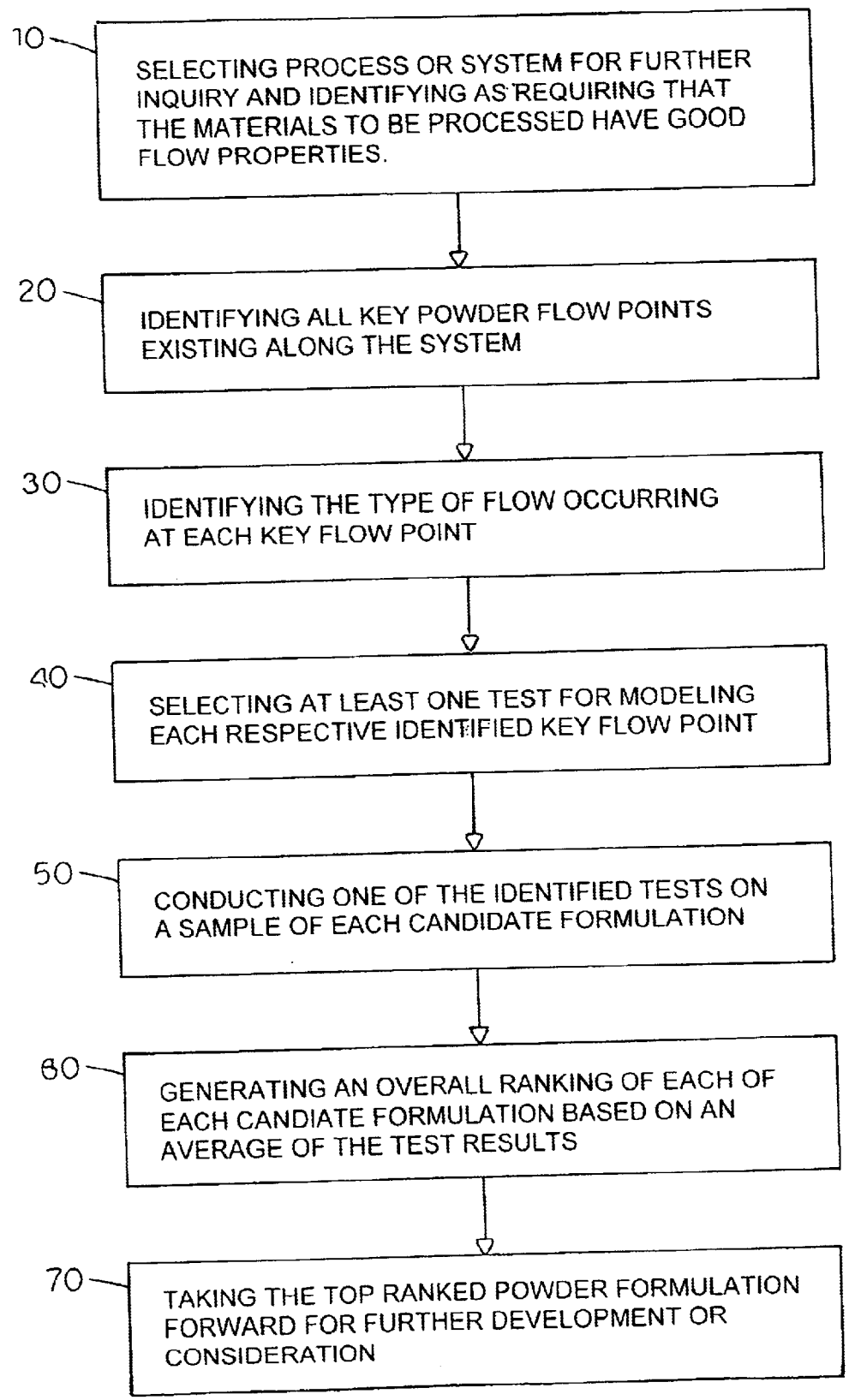
FIG. 1 is a flow diagram representing a number of steps taken in accordance with the present invention.

The generalized method according to the present invention will now be described with reference to the flow diagram of FIG. 1. The researcher or scientist is initially presented with certain initial factors or considerations. Thus, in step 10, a process or system is selected for further inquiry and identified as requiring that the materials to be processed thereby have good flow properties. For purposes of the present disclosure, the terms "process" and "system" are used interchangeably. In connection with the identified system, the researcher is presented with a group of pharmaceutical powder blends which are selected as candidate formulations for a future pharmaceutical product to be processed by that particular system. For example, the candidate formulations might contain the same amount of active ingredient or the same ratio of active ingredients, but differ with respect to the amounts or types of excipients or other inactive ingredients.

In step 20, the researcher considers the system under inquiry and identifies all key powder flow points existing along the system, i.e., locations at which poor flow characteristics can be expected to adversely affect the successful operation of the system. Next, in step 30, the researcher identifies the type of flow occurring at each key flow point (e.g., funneling, tumbling, avalanching, dropping, turbulent flow, laminar flow, and the like). In step 40, the researcher selects from the universe of available flow tests and methodologies (either conventional tests such as those described hereinabove or new, as yet unavailable tests) at least one test deemed to be relevant and appropriate for modeling powder flow at one of the key flow points. In this manner, a test is selected for modeling each respective identified key flow point. At this stage, a plurality of key flow points are thus identified and at least one relevant test is associated with each of those key flow points. Subsequently, the researcher in step 50 conducts one the identified tests on a sample of each candidate formulation. This step is repeated as necessary such that each key flow point is modeled by its corresponding test and each candidate formulation is tested at each key flow point. As a result, the researcher generates an array of flow performance data for each candidate formulation as tested by each test.

For each key flow point modeled, it will be apparent from the test data which candidate formulation expresses the best flow properties. It would not be surprising that the test data show that one given powder formulation offers the best flow properties at one key flow point of the system (e.g., flow out of a hopper) while offering mediocre or even the worst flow properties at another key flow point (e.g., flow from a feed frame into a die cavity). Accordingly, in step 60, the researcher generates an overall ranking of each candidate formulation based on an average of the test results. A number of methodologies derived from experimental analysis and/or statistics could be employed to generate the overall ranking. The following equation, however, has been found to be suitable in conjunction with the present invention:

overall rank for powder $(X)$=[Test #1 score×$(1/N)$]+[Test #2 score×$(1/N)$]+J+[Test #$N$ score×$(1/N)$], where (X) designates one of the material samples tested; "N" represents the total number of tests conducted; "Test #1 score" is the test result value obtained from conducting the first flow test corresponding to the first key flow point identified; "Test #2 score" is the test result value obtained from conducting the second flow test corresponding to the second key flow point identified; and "Test #N score" is the test result value obtained from conducting the last or $N^{th}$ flow test corresponding to the last or $N^{th}$ key flow point identified.

As an additional step, the researcher could make the determination that one or more of the key flow points are more or less important or significant with respect to the other key flow points. In such a case, the researcher could either discount or emphasize one or more of the tests conducted by assigning skewed weightings to the test results, and then calculating the overall ranking based on a weighted average. For instance, in a case where three key flow points (1), (2) and (3) have been modeled, the test results for (1) might be discounted by 20%, the results for (2) kept at an equal weighting, and the results for (3) discounted by 3%.

In any case, the end result will be that an overall ranking is calculated for each candidate formulation, and the formulation with the highest overall ranking will be determined as exhibiting the best overall flow properties for the entire system under inquiry. Therefore, as a final step 70, the researcher takes the top ranked powder formulation forward for further development or consideration, since the method of the present invention demonstrated that this particular formulation will have the best flow and greatest potential for success during processing through the system.

A simplified example of an implementation of the inventive process will now be described.

EXAMPLE OF USE

Figure 2:
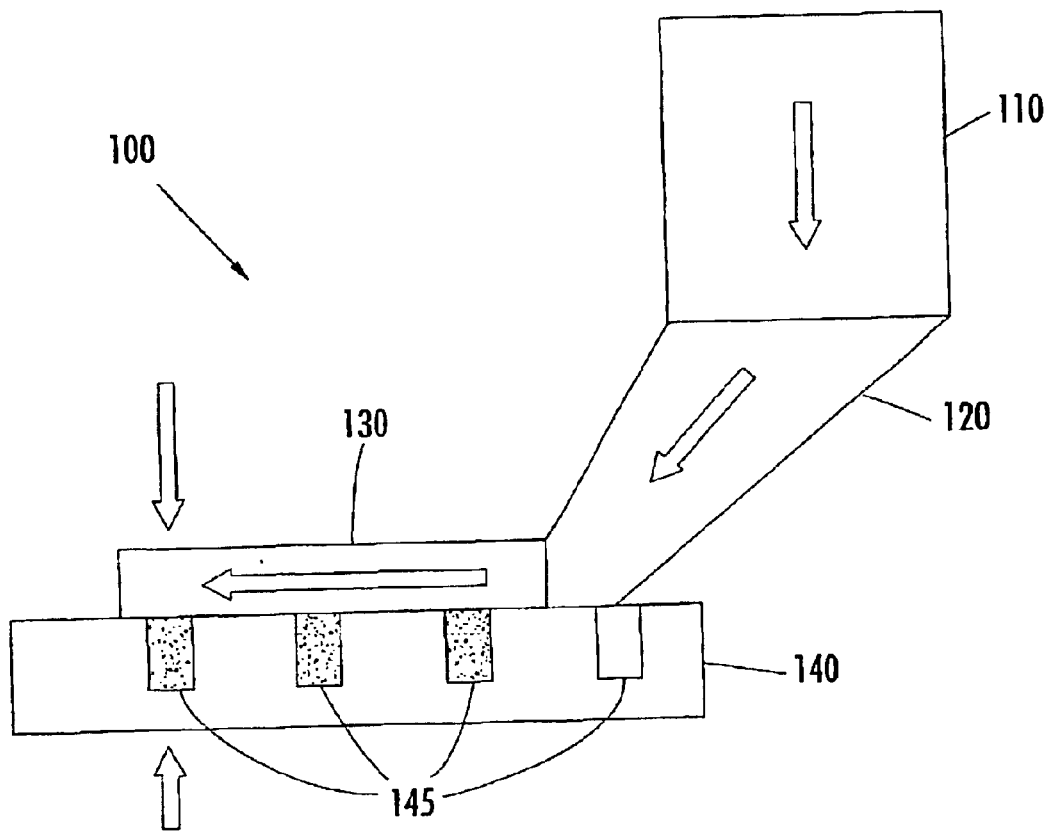
FIG. 2 is a simplified diagram of an exemplary apparatus which can be modeled by the present invention.

Three powder blend formulations, hereinafter designated Powders A, B and C, were developed and considered by the researcher or scientist for a potential new pharmaceutical product. It was then decided that the process of compressing of each blend into tablets on a small scale should be conducted in order to determine the best candidate for further scaled-up (and more costly) development. Referring to the simplified diagram of FIG. 2, a rotary tablet press generally designated 100, such as a MANESTY BETAPRESS apparatus, was selected for use in carrying out the compression process, particularly because rotary table press 100 has been determined to be similar to tablet presses commonly used on a large production scale. Rotary tablet press 100 generally includes a hopper having a cylindrical portion 110 and an attached funnel portion 120, a feed frame 130, and a die table 140 including a plurality of round die cavities 145. Die table 140 is typically circular, stainless steel, rotating device. For the operation of rotary table press 100 to be successful, a good powder flow is required at all salient points of the system, and consequently stoppages due to flooding, starving or erratic behavior is unacceptable. In addition, it is essential that the tablets formed by rotary tablet press 100 exhibit good uniformity in weight. Thus, each die cavity 145 must be consistently, accurately and completely filled with pharmaceutical product. Such results will be ensured by effecting a good flow of powder.

The process or system requiring materials with good flow properties was thus identified as being a powder compression process wherein some known, large-scale tablet press apparatus is to be utilized, and of which rotary table press 100 is representative. Next, the researcher identified the key powder flow points for rotary tablet press 100 as being (1) flow out of hopper 110 and 120 (2) flow in feed frame 130, and (3) flow from the powder bed in feed frame 130 into die cavities 145 of die table 140. This identification was based on the experience and scientific judgment of the researcher, but could have been based on other means.

The researcher then identified the type of flow occurring at each key flow point as being (1) the funneling action of the powder blends out of hopper 110 and 120 (e.g., the hopper angle and geometry are considered to be important), (2) the avalanching and tumbling of the powder bed in feed frame 130, and (3) the dropping of small masses or "plugs" of the powder blend from feed frame 130 into die cavities 145 under the influence of gravity.

The researcher subsequently selected the relevant tests to be employed for the purpose of modeling each type of flow identified at each key flow point. As described above, the particular test selected can be either a conventional test or some new, heretofore undeveloped test. With respect to the funneling flow, the researcher determined that no standard test existed to account for the funneling flow occurring in uniquely shaped hopper 110 and 120 of exemplary rotary table press 100. Accordingly, an exact scaled-down version of hopper 110 and 120 was constructed, and special software was written to run on a computer interfaced with a standard top loading balance. When powder flows out of the small test funnel, the weight delivered to the balance is captured in 0.5 second intervals. Flow versus time is plotted and the maximum rate of flow is calculated.

The researcher also determined that the avalanching and tumbling actions occurring in feed frame 130 could best be simulated by the Amherst Process Instruments AERO-FLOW™ device which measures, based on deterministic chaos theory, the time interval of a series of avalanches of the test powder to assess the powder flowability. The researcher further determined that the powder drop in feed frame 130 as a plug into die cavity 145 can be best simulated by a Hanson Research FLODEX™ device, which is a powder flowability index test instrument that measures the smallest diameter of a circular opening of interchangeable discs through which a bed of powder flows without interruption. The test bed rests on top of a flat disc with a circular opening, and the powder drops through by gravity.

The researcher then conducted the identified tests on a sample of each candidate powder blend (Powders A, B and C) being considered for the system. The results were tabulated as follows:

TABLE 1

| Powder | Funnel test results (g/s) | Aero-Flow ™ results (mean time, s) | Flodex ™ results (mm) |
|---|---|---|---|
| A | 12.0 | 8.7 | 24 |
| B | 15.5 | 6.4 | 18 |
| C | 18.6 | 5.5 | 20 |

Using the tabulated data, the researcher ranked each powder blend based on a weighted average of the test results (equal or skewed depending on the relative importance of each key powder flow point, and normalized the results such that a value of 1.0 would indicate the best powder for the given key flow point (i.e., 1.0=best).

For the funnel test, hereinafter referred to as Test #1, a higher flow rate is indicative of better powder flow. Considering data from Table 1 above that Powder C exhibited the best flow, the normalized rankings for the funnel test were calculated as follows:

Powder C: 18.6/18.6=1.0 (best)
Powder B: 15.5/18.6=0.83 (intermediate)
Powder A: 12.0/18.6=0.65 (worst)

For the AERO-FLOW™ test, hereinafter referred to as Test #2, a smaller mean time to avalanche is indicative of better powder flow, such that Powder C again exhibited the best flow. The normalized rankings for avalanching were thus calculated as follows:

Powder C: 5.5/5.5=1.0 (best)
Powder B: 5.5/6.4=0.86 (intermediate)
Powder A: 5.5/8.7=0.63 (worst)

For the FLODEX™ test, hereinafter referred to as Test #3, the ability to flow through a smaller orifice diameter is indicative of better powder flow, such that Powder B exhibited the best flow. The normalized rankings in this case were calculated as follows:

Powder B: 18/18=1.0 (best)
Powder C: 18/20=0.9 (intermediate)
Powder A: 18/24=0.75 (worst)

The researcher next determined (again based on experience and scientific judgment, although other means could have been employed) that all three key flow points, having at this point been identified and modeled for the system under present inquiry, were equally important in the present system. Accordingly, the researcher accorded each key flow point (and the test data resulting therefrom) an equal weighting, i.e., 33.3% each. The researcher then calculated the overall rank for each candidate powder blend according to the following equation:

overall rank for powder (X)=[Test #1 score×0.333]+[Test #2 score×0.333]+[Test #3 score×0.333].

Since the test scores obtained in the present example have been normalized, the best possible score for any given powder would be 1.0. The calculations of overall rank for Powders A, B, and C were thus as follows:

Powder C: [1.0×0.333]+[1.0×0.333]+[0.9×0.333]=0.97 (best)
Powder B: [0.83×0.333]+[0.86×0.333]+[1.0×0.333]=0.90
Powder A: [0.65×0.333]+[0.63×0.333]+[0.75×0.333]= 0.68 (worst)

These results clearly indicate that, when each key flow point is considered in the context of the entire system, Powder C is clearly the top ranked powder. According to the method of the present invention, this top ranking indicates to the researcher that the formulation for Powder C will express the best flow characteristics, and thus have the greatest potential for success in the development of a new pharmaceutical product, if that formulation is to be processed during the compression stage of a large-scale tablet manufacturing system using a rotary tablet press operating with the same principles as rotary tablet press 100 exemplified hereinabove. The formulation for Powder C would thus be taken forward for further development.

The overall ranking obtained from employing the above-described methodology, i.e., A<B<C, was compared to the results of actual, production-scale tableting press runs with each of Powders A, B and C. The actual flow behavior exhibited by Powders A, B and C during tableting was determined by measuring tablet weight uniformity. These actual test runs confirmed the validity of the overall ranking. As described above, some of the individual tests (e.g., the FLODEX™ test) conducted at different key flow points, when considered in isolation, did not accurately predict the correct overall ranking of A<B<C for the tablet compression system. Other conventional tests were conducted for further comparison, and also demonstrated the inferiority of relying on a single test to model powder flow for a multi-step system. Specifically, calculation of the Hausner ratio for each of Powders A, B and C resulted in an incorrect overall ranking of A<C<B, and calculation of the angle of repose resulted in an incorrect overall ranking of C<B<A.

The method according to the present invention therefore provides an effective tool for the pharmaceutical scientist to assist with the development of robust and efficient processes which require good powder flow. The method gives a more accurate prediction of the flow properties of powders and powder formulations by modeling the kinds of flow actually occurring in the system. The holistic approach taken by the invention is based on relevant assessments made at key steps of a given system, instead of an examination based only on single, conventional tests that might not be directly relevant with respect to the entire system. The invention can also be used for troubleshooting existing processes if a change in powder material properties is suspected. Comparison with known reference materials can be carried out. In addition, improvements or modifications to existing processes can be examined by utilizing the present invention to assess changes made to formulations and the resultant impact on flowability.

It will be understood that the applications of the present invention are not limited to examination of tablet compression, but extend to all operations involving the processing of powders.

It will be further understood that various details of the invention may be changed without departing from the scope of the invention. Furthermore, the foregoing description is for the purpose of illustration only, and not for the purpose of limitation—the invention being defined by the claims.

What is claimed is:

1. A method for predicting flow properties of one or more materials proposed for processing in a system which requires good flow properties to operate successfully, the method comprising the steps of:

(a) identifying a plurality of key flow points along a system;

(b) for each key flow point, characterizing a type of flow occurring at that key flow point;

(c) for each key flow point, selecting a flow test relevant for modeling the type of flow occurring at that key flow point;

(d) providing a plurality of material samples wherein each material sample has a different composition, blend and/or concentration of ingredients;

(e) for each key flow point, modeling the type of flow occurring at that key flow point by conducting the flow test selected for that key flow point on each material sample to produce a plurality of test result values, wherein each test result value is a function of one of the flow tests conducted and of the material sample tested by that flow test; and (f) ranking each material sample based on a calculated average of the test result values to determine which of the material samples tested has optimal overall flow properties for the system as compared against the other material samples.

2. The method according to claim 1 wherein each material sample is a powder sample.

3. The method according to claim 2 wherein each powder sample is a pharmaceutical powder sample.

4. The method according to claim 3 wherein each pharmaceutical powder sample includes active and inactive ingredients.

5. The method according to claim 1 wherein the plurality of test result values produced by conducting the selected flow tests is utilized to generate a ranking of the material samples from best to worst flow properties for each flow test conducted.

6. The method according to claim 5 comprising the step of normalizing the test result values for each flow test conducted by adjusting the test result value having the best ranking by a factor that sets that test result value to unity, and adjusting the other test result values obtained from that flow test by the same factor to convert the other test result values to reduced values equal to less than unity.

7. The method according to claim 1 wherein the step of ranking each material sample based on a calculated average of the test result values includes calculating an overall ranking of each material sample according to the following equation:

$$\text{overall rank for powder } (X) = [\text{Test \#1 score} \times (1/N)] + \ldots + [\text{Test \#N score} \times (1/N)],$$

wherein (X) designates one of the material samples tested; N represents the total number of flow tests conducted; Test #1 score is the test result value obtained from conducting a first one of the plurality of flow tests corresponding to a first one of the key flow points identified; and Test #N score is the test result value obtained from conducting an $N^{th}$ one of the plurality of flow tests corresponding to an $N^{th}$ one of the key flow points identified.

8. The method according to claim 7 comprising the steps of determining that one or more of the key flow points identified is less significant than one or more of the other key flow points and, for each material sample tested, multiplying the test result value corresponding to the less significant key flow point by a factor reflecting the lesser significance.

9. The method according to claim 1 comprising the step of assigning a weighting factor to the test result value produced by each flow test conducted, wherein the weighting factor is based on an assessed significance of the key flow point modeled by that flow test relative to the other key flow points identified for the system, and wherein the step of ranking each material sample is based on a weighted average of the test result values.

10. The method according to claim 9 wherein each assigned weighting factor is equal to the other assigned weighting factors.

11. The method according to claim 9 wherein at least one of the assigned weighting factors is skewed with respect to one or more of the other assigned weighting factors.

12. The method according to claim 9 wherein the system includes a powder tablet forming process and the plurality of flow tests include powder flow tests.

13. A method for predicting flow properties of one or more materials proposed for processing in a system which requires good flow properties to operate successfully, the method comprising the steps of:

(a) identifying a plurality of key flow points along a system;

(b) for each key flow point, characterizing a type of flow occurring at that key flow point;

(c) for each key flow point, selecting a flow test relevant for modeling the type of flow occurring at that key flow point;

(d) providing a plurality of material samples wherein each material sample has a different composition, blend or concentration of ingredients;

(e) for each key flow point, modeling the type of flow occurring at that key flow point by conducting the flow test selected for that key flow point on each material sample to produce a plurality of test result values, wherein each test result value is a function of one of the flow tests conducted and of the material sample tested by that flow test; and (f) generating an overall ranking each of material sample to predict the flow properties that each material sample will exhibit during processing of the material sample in the system by utilizing the following equation:

$$\text{overall rank for powder } (X) = [\text{Test \#1 score} \times (1/N) \times WF_1] + \ldots + [\text{Test \#N score} \times (1/N) \times WF_N],$$

wherein (X) designates one of the material samples tested; N represents the total number of flow tests conducted; Test #1 score is the test result value obtained from conducting a first one of the plurality of flow tests corresponding to a first one of the key flow points identified; $WF_1$ is a weighting factor optionally assigned to the Test #1 score based on an assessed significance of the first key flow point relative to the other key flow points; Test #N score is the test result value obtained from conducting an $N^{th}$ one of the plurality of flow tests corresponding to an $N^{th}$ one of the key flow points identified; and $WF_N$ is a weighting factor optionally assigned to the Test #N score based on an assessed significance of the $N^{th}$ key flow point relative to the other key flow points.

14. A method for predicting flow properties of one or more powder formulations proposed for processing in a system which requires good powder flow properties to operate successfully, the method comprising the steps of:

(a) identifying a plurality of key powder flow points along a system;

(b) for each key flow point, characterizing a type of flow occurring at that key flow point;

(c) for each key flow point, selecting a powder flow test relevant for modeling the type of flow occurring at that key flow point;

(d) providing a plurality of powder samples wherein each powder sample has a different composition, blend and/or concentration of ingredients;

(e) for each key flow point and for each powder sample, modeling the type of flow occurring at that key flow point by conducting the powder flow test selected for that key flow point to produce a plurality of test result values, wherein each test result value is a function of one of the powder flow tests conducted and of the powder sample tested by that powder flow test; and (f) ranking each powder sample based on a calculated average of the test result values to determine which of the powder samples tested has optimal overall flow properties for the system as compared against the other powder samples.

15. The method according to claim 14 wherein at least one of the identified key flow points is characterized by a funneling process.

16. The method according to claim 14 wherein at least one of the identified key flow points is characterized by an avalanching process.

17. The method according to claim 14 wherein at least one of the identified key flow points is characterized by a tumbling process.

18. The method according to claim 14 wherein at least one of the identified key flow points is characterized by a powder plug dropping process.

19. The method according to claim 14 wherein the plurality of powder flow tests selected is a funneling flow-type test.

20. The method according to claim 14 wherein the plurality of powder flow tests selected employs an AEROFLOW-type device.

21. The method according to claim 14 wherein the plurality of powder flow tests selected employs a FLODEX-type device.

22. The method according to claim 14 wherein the system includes a tablet forming system including a hopper, a funnel fluidly communicating with the hopper, a feed frame fluidly communicating with the funnel, and a die table fluidly communicating with the feed frame.

23. A ranking process for determining an optimized powder formulation which forms a pharmaceutical product, the powder formulation predicted to exhibit optimized powder flow in a pharmaceutical product manufacturing system, the ranking process comprising the steps of:

(a) identifying a plurality of key powder flow points along a pharmaceutical product manufacturing system;

(b) for each key flow point, characterizing a type of flow occurring at that key flow point;

(c) for each key flow point, selecting a powder flow test relevant for modeling the type of flow occurring at that key flow point;

(d) providing a plurality of sample powder formulations wherein each sample formulation has a different composition, blend and/or concentration of ingredients;

(e) for each key flow point and for each sample formulation, modeling the type of flow occurring at that key flow point by conducting the powder flow test selected for that key flow point to produce a plurality of test result values, wherein each test result value is a function of one of the powder flow tests conducted and of the sample formulation tested by that powder flow test; and (f) determining the optimized powder formulation by ranking each sample formulation based on a calculated average of the test result values to determine which of the sample formulations tested has optimal overall flow properties for the system as compared against the other sample formulations.

* * * * *